United States Patent [19]

Holden

[11] 4,206,210

[45] Jun. 3, 1980

[54] ALKYLTHIO-7,8-DIHDROXY-1-PHENYL-2,3,4,5-TETRAHYDRO-1H-3-BENZAZEPINES HAVING DOPAMINERGIC ACTIVITY

[75] Inventor: Kenneth G. Holden, Haddonfield, N.J.

[73] Assignee: SmithKline Corporation, Philadelphia, Pa.

[21] Appl. No.: 912,131

[22] Filed: Jun. 2, 1978

Related U.S. Application Data

[63] Continuation-in-part of Ser. No. 760,500, Jan. 19, 1977, abandoned.

[51] Int. Cl.$^2$ .................... A61K 31/55; C07D 223/16
[52] U.S. Cl. ........................... 424/244; 260/239 BB
[58] Field of Search .............. 260/239 BB; 424/244

[56] References Cited

U.S. PATENT DOCUMENTS

| | | | |
|---|---|---|---|
| 3,393,192 | 7/1968 | Walter et al. | 260/239 BB |
| 3,483,185 | 12/1969 | Tokolics et al. | 260/239 BB |

Primary Examiner—Donald G. Daus
Assistant Examiner—D. B. Springer
Attorney, Agent, or Firm—William H. Edgerton

[57] ABSTRACT

A new series of lower alkylthio-7,8-dihydroxy-1-phenyl-2,3,4,5-tetrahydro-1H-3-benzazepines having potent central dopaminergic activity of utility in treating Parkinson's disease. The 6-and 9-methylthio compounds are particularly of use.

17 Claims, No Drawings

ALKYLTHIO-7,8-DIHDROXY-1-PHENYL-2,3,4,5-TETRAHYDRO-1H-3-BENZAZEPINES HAVING DOPAMINERGIC ACTIVITY

This application is a continuation-in-part application of copending Ser. No. 760,500 filed Jan. 19, 1977, now abandoned.

This invention comprises a new group of chemical compounds which are 1-phenyl-2,3,4,5-tetrahydro-1H-3-benzazepines having three substituents on the benz-ring of the nucleus, one of which is preferably a 6-lower alkylthio group. The compounds have utility as dopaminergic agents with pronounced activity at central nervous system receptors.

Exemplary of the compounds of this invention are those represented by the following structural formula:

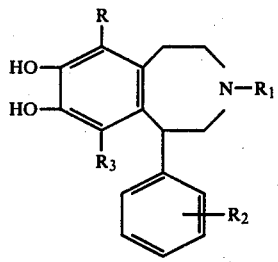

in which:

R and $R_3$ are hydrogen, lower alkylthio of 1-5 carbon atoms or trifluoromethylthio, at least one of R and $R_3$ being a group other than hydrogen;

$R_1$ is hydrogen, lower alkyl of 1-5 carbons, hydroxyethyl, lower alkenyl of 3-5 carbons, benzyl, phenethyl, carbobenzoxy or lower alkanoyl of 1-5 carbons; and $R_2$ is hydrogen, halo such as fluoro, chloro, bromo or iodo, trifluoromethyl, methyl, methoxy or hydroxy.

The compounds in which $R_1$ is benzyl, phenethyl, carbobenzoxy or lower alkanoyl or the higher alkoxy or acyloxy containing compounds are of utility particularly for intermediate use in the preparation of other more active compounds.

Also included in this invention are the S-oxidized derivatives of the compounds of Formula I that is the 6 or 9-lower alkylsulfonyl, lower alkylsulfinyl, trifluoromethylsulfonyl, trifluoromethylsulfinyl or dimethylsulfonium halide containing compounds. These are the compounds defined in Formula I in which at least one of R and $R_3$ is a methyl or trifluoromethyl sulfoxide or sulfonyl group together with the sulfonium derivatives (those in which R or $R_3$ are —(CH$_3$)$_2$SO$_2$X where X is a pharmaceutically acceptable anion such as chloride, bromide, iodide, tosylate or mesylate).

A subgeneric group of compounds with within the above illustrative group are those of Formula I in which R is methylthio or trifluoromethylthio, $R_1$ and $R_3$ are hydrogen. In this group individual compounds of note are those in which $R_2$ is hydrogen, chloro, methyl, trifluoromethyl, methoxy or hydroxy. The 9-methylthio containing compounds while less potent than the 6-methylthio compounds have fewer side effects.

The pharmaceutically acceptable acid addition salts having the utility of the free bases of Formula I, prepared by methods well known to the art, are formed with both inorganic or organic acids, for example: maleic, fumaric, benzoic, ascorbic, pamoic, succinic, bismethylenesalicylic, methanesulfonic ethanedisulfonic, acetic, oxalic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids. Similarly the quarternary salts including the sulfonium derivatives as defined above include those prepared from organic halides such as lower alkyl halides, for example, methyl bromide, methyl iodide, ethyl iodide, benzyl chloride, as well as methyl tosylate or mesylate and the like.

Certain 1-phenyl-2,3,4,5-tetrahydro-1H-3-benzazepines have been described in U.S. Pat. No. 3,393,192; 3,795,683; British Pat. No. 1,118,688; and Swiss Pat. No. 555,831, including general methods of preparation. However these references disclose no benztrisubstituted compounds of the type here claimed, no 6-methylthio substituted compounds of any kind and no advantage to such 6-methylthio substitution in the structures. These references do disclose 7,8-dihydroxy substituted-1-phenyl-3-benzazepines and various intermediates therefor, some of which serve as starting materials for preparing the compounds of this invention.

It will be obvious to one skilled in the art that the compounds of Formula I may be present as diastereo isomers which may be resolved into d or l optical isomers. Resolution of the optical isomers may be conveniently accomplished by factional crystallization of their salts with optically active acids from appropriate solvents. Unless otherwise specified herein or in the claims, it is intended to include all isomers, whether separated or mixtures thereof. Where isomers are separated, the desired pharmacological activity will often predominate in one of the isomers usually in the d-isomer.

The compounds of Formula I contain as one skilled in the art will recognize two functional hydroxy groups at positions 7 and 8 which may be optionally converted to the lower alkoxy derivatives of 1-5 carbons in each alkoxy group such as methoxy, ethoxy, butoxy or isoamyloxy or the lower alkanoyloxy derivatives of 2-5 carbons such as O-acetyl, O-propionyl or O-valeryl. The dimethoxy or diacetoxy derivatives are most useful but are of somewhat lower level of general biological activity. The diacyloxy derivatives in general have substantial oral activity.

The lower alkyl or lower alkanoyl derivatives of the compounds of Formula I are prepared by alkylation-acylation methods which are conventional to the art. One skilled in the art, however, would recognize that the use of lower alkyl halides as alkylating agents, for example, in addition to O-alkylation would also form the lower alkylsulfonium halides at the sulfur atom during the alkylation. For example, the dimetylsulfonium bromide would form during reaction with methyl bromide. These sulfonium salts can optionally be reconverted to the parent thio compound without affecting the O-alkyl groups by conventional methods such as heating in 1 N hydrobromic acid, in brine or another source of bromide or chloride ions.

The compounds of Formula I may be prepared by the cyclization reactions described in U.S. Pat. No. 3,393,192 using as starting materials an appropriate 2-lower alkylthio-3,4-dimethoxyphenethylamine or the corresponding phenethylaminomethylbenzyl alcohol. The N-substituted derivatives of Formula I may also be prepared using the appropriate tertiary amino alcohol in the cyclization reaction. A preferred method of preparation, however, is to react a 7,8-dione of the formula:

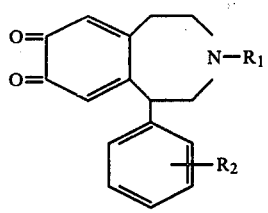

with the desired mercaptan (RSH) in a suitable inert organic solvent such as an alcoholic solvent, methanol or ethanol, at about room temperature to give a compound of the following structure:

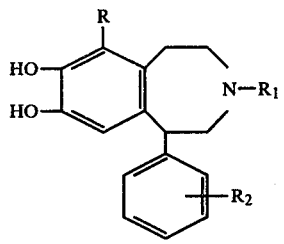

In the addition reaction noted above the 9-isomer is also obtained, however, the mixture is easily separated into the 6 and 9-isomers by methods described hereafter. Also the mixture of monosubstituted isomers can be alternatively used to prepare the 6,9-disubstituted congeners as described immediately hereafter.

A second lower alkylthio substituent can optionally be introduced into the 9-position by oxidation of III (or into 6 via the 9-isomer) with 2,3-dichloro-5,6-dicyano-1,4-benzoquinone followed by reaction once more with the desired mercaptan. In the intermediates of Formulas II and III, R, $R_1$ and $R_2$ are as defined for compounds of Formula I.

The important 7,8-dialkoxy derivatives are also conveniently prepared by reacting a 6-lithium derivative corresponding to Formula I (R=Li) with the appropriate lower alkyl or trifluoromethyldisulfide in an inert organic solvent in which the reactants are soluble such as ether or tetrahydrofuran at ambient or elevated temperature under anhydrous conditions. The important 7,8-dimethoxy derivatives may be optionally prepared by reaction of the 7,8-dihydroxy congener with diazomethane. Of course the dialkoxy derivatives are also conveniently prepared by the conventional cyclization reaction mentioned above.

The sulfonyl derivatives of the compounds of Formula I [I in which R and/or $R_3$ are lower alkyl or trifluoromethyl sulfonyl (alk$SO_2$— or $CF_3SO_2$—)] are prepared by oxidizing the corresponding sulfide optionally protected at the N or 3-position by an inert group such as trifluoroacetyl or carbobenzoxy using a sulfonyl producing oxidizing agent such as excess hydrogen peroxide, m-chloroperbenzoic acid, peracetic acid or perbenzoic acid. The 6-sulfinyl derivatives of the compounds of Formula I [I in which R and/or $R_3$ are lower alkyl or trifluoromethyl sulfinyl (alkSO- or $CF_3SO$-)] are prepared using a sulfoxide producing oxidizing agent such as sodium periodate usually in neutral solution or one equivalent of hydrogen peroxide or m-chloroperbenzoic acid at low temperatures.

The compounds of Formula I, their lower alkyl ethers or esters and their nontoxic pharmaceutically acceptable addition salts have a novel dopaminergic effect. It is well known that dopaminergic compounds have a dual effect on dopamine receptors in the central nervous system notably the brain as well as on peripheral dopamine receptors such as those affecting the peripheral cardiovascular system.

The latter effect results in increased renal blood flow with a resulting hypotensive effect. It is often measured by administering the compound by infusion i.v. incrementally at five minute intervals to the anesthetized normotensive dog with measurement of various cardiovascular parameters. The effect on renal vasculator resistance can be calculated from any change in renal blood flow and arterial blood pressure. The effect is quantified as an $ED_{15}$ values which is the cumulative dose which produces a 15% decrease in renal vascular resistance (R=B.P. in mm/Hg./B.F. ml/min.).

The 6-lower alkylthio containing benzazepine compounds of Formula I especially have antiparkinsonism activity due to central dopaminergic activity a demonstrated by employing a modified standard animal pharmacological test procedure reported by Ungerstedt et al., in *Brain Research* 24, 1970, 485–493. This procedure is based on a drug induced rotation of rats having extensive unilateral lesions of the substantia nigra. Briefly, the test comprises the quantitative recording of rotational behavior in rats in which 6-hydroxydopamine lesions of the nigrostriatal dopamine system have been produced. A unilateral brain lesion in the left substantia nigra causes the dopamine receptor in the left caudate to become hypersensitive following the resulting degeneration of the nigral cell bodies. These lesions destroy the source of the neutrotransmitter dopamine in the caudate but leave the caudate cell bodies and their dopamine receptors intact. Activation of these receptors by drugs which produce contralateral rotation, with respect to the lesioned side of the brain, is used as a measure of central dopaminergic activity of the drug.

Compounds which are known to be clinically effective in controlling parkinsonism, such as, for example, L-dopa and apomorphine, are also effective in this rate turning model. These compounds directly activate the dopamine receptors and cause contralateral rotation of the lesioned rat.

Rotational activity is defined as the ability of a compound to produce 500 contralateral rotations during a two-hour period after administration, usually intraperitoneally. The dose corresponding to 500 contralateral rotations per two hours is obtained and assigned as the $RD_{500}$ value.

The unexpected nature of the biological spectrum of the dopaminergic compounds of Formula I is a shift from activity at peripheral receptors to central activity. For example, 7-8-dihydroxy-6-methylthio-1-phenyl-2,3,4,5-tetrahydro-3-1H-benzazepine hydrobromide has an $RD_{500}$ of 0.18 (0.06–0.29) mg/Kg [0.14 mg/Kg base] which is 8 times more potent than is its 6-hydrogen analog with a faster onset and longer duration of activity. The $ED_{15}$ of this compound is 372 which is 10 times less potent than the 6-hydrogen analog. 7,8-Dihydroxy-9-methylthio-1-phenyl-2,3,4,5-tetrahydro-3-1H-benzazepine hydrobromide has an $RD_{500}$ of 4.8 mg/Kg [3.8 base] which is 3 times more potent than the 6-hydrogen analog. The higher alkylthio, i.e. those other than methylthio as well as the 6,9-disubstituted congeners were less potent in the rotation test than the preferred methylthio containing compounds.

The pharmaceutical compositions of this invention having dopaminergic activity are prepared in conventional dosage unit forms by incorporating a compound of Formula I, an isomer or a pharmaceutically acceptable acid addition salt thereof, with a nontoxic pharmaceutical carrier according to accepted procedures in a nontoxic amount sufficient to produce the desired pharmacodynamic activity in a subject, animal or human. Preferably the composition will contain the active ingredient in an active but nontoxic amount selected from about 2.5 mg to about 1000 mg of active ingredient per dosage unit but this quantity depends on the specific biological activity desired and the conditions of patient. The most desirable object of the compositions and methods is in the treatment of Parkinson's disease to ameliorate or prevent the attacks common with patients suffering from this central nervous system abnormality.

The pharmaceutical carrier employed may be, for example, either a solid or liquid. Exemplary of solid carriers are lactose, terra alba, sucrose, talc, gelatin, agar, pectin, acacia, magnesium stearate, stearic acid, and the like. Exemplary of liquid carriers are syrup, peanut oil, olive oil, water and the like. Similarly the carrier or diluent may include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form, or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable liquid such as an ampul, or an aqueous or nonaqueous liquid suspension.

The pharmaceutical preparations are made following the conventional techniques of the pharmaceutical chemist involving mixing, granulating and compressing when necessary, or variously mixing and dissolving the ingredients as appropriate to give the desired end product.

The method of producing dopaminergic activity in accordance with this invention as described above comprises administering internally to a subject in need of such activity a compound of Formula I or a pharmaceutically acceptable acid addition salt thereof, usually combined with a pharmaceutical carrier, in a nontoxic amount sufficient to produce said activity as described above. The route of administration may be any route which effectively transports the active compound to the dopamine receptors which are to be stimulated such as orally or parenterally, the oral route being preferred. Advantageously, equal doses will be administered several times such as two or three times a day with the daily dosage regimen being selected from about 150 mg. to about 1.5 g. When the method described above is carried out anti-parkinsonism activity is produced with a minimum of side effects.

The following examples are designed to teach those skilled in the art the preparation and use of the invention. Other modifications of the synthetic procedures and of the structural variations possible will be obvious beyond the teaching of the examples. All temperatures are in degrees Centigrade.

EXAMPLE 1

To a suspension of 7,8-dihydroxy-1-phenyl-2,3,4,5-tetrahydro-1H-3-benzazepine hydrobromide (34 g, 0.101 mole, U.S. Pat. No. 3,393,192) in methanol (275 ml) was added a solution of 2,3-dichloro-5,6-dicyano-1,4-benzoquinone (25.2 g, 0.111 mole) in methanol (125 ml). The addition was carried out rapidly with stirring at 0° under an argon atmosphere. After stirring at 0° for 1 hour the reaction mixture was filtered and the orange precipitate was washed with cold methanol (75 ml), ethyl acetate (100 ml) and then diethyl ether (100 ml). After drying at room temperature under vacuum, 1-phenyl-2,3,4,5-tetrahydro-1H-3-benzazepine-7,8-dione hydrobromide (32.8 g, 0.98 mole, 97%) was obtained, mp 164°–165° (dec.).

Anal. Calc'd for $C_{16}H_{15}NO_2 \cdot HBr \cdot \frac{1}{4}H_2O$; C, 56.34; H, 4.84; N, 4.11. Found: C, 56.02; H, 4.76; N, 4.01.

Into a stirred suspension of 1-phenyl-2,3,4,5-tetrahydro-1H-3-benzazepine-7,8-dione (5 g, 0.015 mole, generated from the salt above) in methanol (150 ml) was rapidly bubbled an excess of methyl mercaptan. The orange quinone quickly dissolved to give a pale yellow solution which was evaporated to a residue (5.5 g) which was a mixture of 7,8-dihydroxy-6-methylthio and 9-methylthio-1-phenyl-2,3,4,5-tetrahydro-1H-3-benzazepine hydrobromides. The 9-isomer could be directly crystallized by dissolving the residue in methanol and diluting to the cloud point with ethyl acetate; however, this material (2.2 g) contained a small amount of the 6-isomer. A more efficient separation was achieved by chromatography on silica gel. A mixture of the isomers (3.3 g) was dissolved in 3.2 ml of methanol and diluted to 80 ml with chloroform. This solution was applied to a silica gel column (100 g, 4.5×15 cm) and eluted with a linear gradient composed of chloroform containing an increasing concentration of methanol (1000 ml, 5% to 20% methanol). The 6-isomer was eluted first followed by a mixture of 6- and 9-isomers and then the 9-isomer. Fractions containing the pure 6-isomer were combined and evaporated to a residue (1.4 g) which was crystallized from ethanol-ethyl acetate to give 0.64 g (0.0017 mole, 11%), mp 258° (dec.).

Anal. Calc'd for $C_{17}H_{19}NO_2S \cdot HBr$: C, 53.41; H, 5.27; N, 3.66; S, 8.39. Found: C, 53.41; H, 5.10; N, 3.55; S, 8.64.

Fractions containing the pure 9-isomer were evaporated to a residue and combined with the 2.2 g obtained by direct crystallization. Recrystallization from methanol-ethyl acetate gave the pure 9-isomer (1.25 g, 0.0034 mole, 22%), mp 270° (dec.).

Anal. Calc'd for $C_{17}H_{19}NO_2S \cdot HBr$: C, 53.41; H, 5.27; N, 3.66; S, 8.39. Found: C, 53.15; H, 5.33; N, 3.58; S, 8.24.

EXAMPLE 2

Preparation of 6- and 9-lower alkylthio-7,8-dihydroxy-2,3,4,5-tetrahydro-1-phenyl-3-1H-benzazepines A 1 l. 3-necked, round bottom flask was equipped with a magnetic stirrer, argon gas inlet and outlet tubes, and a powder addition funnel. The outlet tube was arranged so the exit gas bubbled through a solution of sodium hypochlorite (CLOROX®) to remove entrained mercaptan. To a stirred solution of 3–3.7 ml (0.041–0.07 moles) of the appropriate alkylmercaptan in 300 ml of methanol was added 10 grams (0.03 moles) of 1-phenyl-7,8-dione-2,3,4,5-tetrahydro-3-1H-benzazepine hydrobromide by means of the powder addition funnel. Addition was carried out in portions at such a rate that the initial intensity brick red color of the solution changed to light orange before each subsequent addition. This process normally takes about 10 minutes to complete. The resulting yellowish solution was stirred for an additional 15–30 minutes and was then evaporated under reduced pressure. The oily residue was chromatographed on silica gel, the products being eluted with a gradient of 5–15% methanol in chloroform. The ratio of 6- and 9-isomers is about 1:2 and the 6-isomer is eluted first. However, repeated chromatography is usually necessary in order to obtain a complete separation. Thus, although the crude yield is quite high, the isolated yields of pure isomers are relatively low.

The melting points, analytical values and isolated yields of the separated isomers as the hydrobromide salts are tabulated below.

| Compounds | m.p. | Calcd. | Found | Yield |
|---|---|---|---|---|
| 9-n-BuS- | 191°–2° | C 56.60 | 56.42 | 14.9% |
|  |  | H 6.18 | 6.31 |  |
|  |  | N 3.30 | 3.22 |  |
| 6-n-BuS- | 197° | C 56.60 | 56.94 | 9.6% |
|  |  | H 6.18 | 6.29 |  |
|  |  | N 3.30 | 3.45 |  |
| 9-i-PrS- | 245°–6° | C 55.07 | 54.72 | 25.6% |
|  |  | H 5.95 | 5.79 |  |
|  |  | N 3.38 | 3.30 |  |
| 6-i-PrS | 269°–70° | C 55.61 | 55.38 | 18.7% |
|  |  | H 5.89 | 6.16 |  |
|  |  | N 3.41 | 3.34 |  |
| 9-EtS- | 287° C.(d) | C 54.55 | 54.32 | 13.4% |
|  |  | H 5.59 | 5.71 |  |
|  |  | N 3.53 | 3.20 |  |
| 6-EtS- | 215°–7°(d) | C 54.44 | 54.42 | 15.1% |
|  |  | H 5.59 | 5.72 |  |
|  |  | N 3.53 | 3.21 |  |

A mixture of 10 g. of trifluoromethyldisulfide, a stoichiometric quantity of dithioerythritol in methanol is allowed to stand at room temperature until the reaction is complete. The mixture is then used as the source of trifluoromethylthio in the general procedure outlined above to produce 6-trifluoromethylthio-7,8-dihydroxy-1-phenyl-2,3,4,5-tetrahydro-3-1H-benzazepine hydrobromide.

The bases of the noted salts are obtained by shaking each salt in a dicarbonate-methylene dichloride mixture, separating the organic layer and evaporating the dried organic extract in vacuo.

EXAMPLE 3

A 3.7 g (0.0145 mole) sample of 7,8-dihydroxy-1-phenyl-2,3,4,5-tetrahydro-1H-3-benzazepine free base was slurried in 25 ml. of acetone and 0.07 g (0.016 mole, 10% excess) of ethylene oxide was added and the mixture placed in a pressure bottle and stirred at ambient temperature for ca. 40 hours. The reaction mixture was heated to 60°–80° for thirty minutes, cooled and filtered. Concentration of the filtrate gave 4.5 g of crystalline solid. This was taken up in ethyl acetate, reprecipitated by the addition of ether and converted to its hydrochloride salt by solution in ethanol, addition of ethereal hydrogen chloride and precipitation of the salt by additional ether to give 3.0 g (yield 60%) on drying. Recrystallization from ethanol-ether gave 1.9 g (yield 38%), mp 136°–137° of 7,8-dihydroxy-3-(2-hydroxyethyl)-1-phenyl-2,3,4,5-tetrahydro-1H-3-benzazepine hydrochloride.

The 2-hydroxyethyl compound (1.5 g) is reacted with 2,3-dichloro-5,6-dicyano-1,4-benzoquinone in methanol as in Example 1 to give 3-(2-hydroxyethyl)-1-phenyl-2,3,4,5-tetrahydro-1H-3-benzazepine-7,8-dionehydrobromide. The (1 g) is reacted with methylmercaptan in methanol as in Example 1 to give 6-methylthio-7,8-dihydroxy-3-(2-hydroxyethyl)-1-phenyl-2,3,4,5-tetrahydro-1H-3-benzazepine hydrobromide.

EXAMPLE 4

A 25 g (0.0874 mole) quantity of 2-methoxy-2-(m-trifluoromethylphenyl)ethyl bromide (U.S. Pat. No. 3,226,440) and 75 ml. of 2-(3,4-dimethoxyphenyl)ethylamine were heated at 90°–95° for two hours with stirring under nitrogen. Cooling caused crystallization of 21.3 g of 2-(3,4-dimethoxyphenyl)-ethylamine hydrobromide. This was filtered and the filtrate fractionally distilled under vacuum. The fraction boiling at 207°–232° C. (1.3–2.0 mm) was collected and the hydrochloride salt formed in ether. This was recrystallized from acetonitrile/ether to give 14.5 g (40% yield) of N-[2-methoxy-2-(m-trifluoromethylphenyl)ethyl]-N-2-(3',4'-dimethoxyphenyl)-ethylamine hydrochloride, m.p. 157°–160°.

A 1.0 g (0.00238 mole) sample of this material was added to 20 ml 48% hydrobromic acid and the mixture heated at reflux for one hour with stirring under nitrogen. The solution was cooled, concentrated to dryness under reduced pressure and the residue triturated with ether to give 1.0 g of crystalline solid (yield, 89%). This was recrystallized from ethanol/ether to give 7,8-dihydroxy-1-(m-trifluoromethylphenyl)-2,3,4,5-tetrahydro-1H-3-benzazepine hydrobromide of mp 153° (forms glass).

The base (1 g) is reacted with 2,3-dichloro-5,6-dicyano-1,4-benzoquinone in methanol to give the dione which (0.5 g) is reacted with methyl mercaptan to give 6-methylthio-7,8-dihydroxy-1-(m-trifluoromethylphenyl)-2,3,4,5-tetrahydro-1H-3-benzazepine hydrobromide.

EXAMPLE 5

Sodium hydride (57%) (4.84 g., 0.115 mole) previously washed with hexane was stirred with dry dimethylsulfoxide (70 ml) at 65°–70° for 2 hours under argon. The mixture was diluted with dry THF (70 ml), cooled to −5° and trimethylsulfonium iodide (23.5 g, 0.115 mole) in 100 ml of dry DMSO was added over a period of 3 minutes. After stirring for one minute o-tolualdehyde (11.5 g, 0.0926 mole) was added at a moderate rate while keeping the reaction mixture at 0° to −5°. The mixture was stirred at 0° for 5 minutes and at room temperature for 1 hour, diluted with 500 ml of ice water and extracted three times with ether. The ether solution was washed with saturated sodium chloride, dried with sodium sulfate and evaporated to an oil which was distilled under reduced pressure (~0.25–0.50 mm) to give 10.25 g (83%) of o-methylstyrene oxide as a clear liquid (b.p. 35°–38°).

Homoveratrylamine (13.6 g, 0.0753 mole) and o-methylstyrene oxide (10.1 g, 0.0753 mole) were stirred at 100° under argon for 16 hours and then diluted with benzene and hexane and cooled in ice. The solid which precipitated was filtered and recrystallized from benzene-hexane to give 8.6 g (36%) of 2-methyl-α-[N-(3,4-dimethoxyphenethyl)aminomethyl]benzyl alcohol, mp 91°–94°.

2-Methyl-α-[N-(3,4-dimethoxyphenethyl)aminomethyl]-benzyl alcohol, (8.5 g, 0.0269 mole), was refluxed in 48% HBr (58 ml) for 2 hours under argon. After cooling the product was filtered off and recrystallized once from ethanol-ethyl acetate to give 6.7 g (69%) of 1-(2-methylphenyl)-7,8-dihydroxy-2,3,4,5-tetrahydro-1H-3-benzazepine hydrobromide which analyzed for a ½ hydrate, mp 232°–233° C.

This compound (5 g) is oxidized using the 1,4-benzoquinone as in Example 1 to give 1-(2-methylphenyl)-2,3,4,5-tetrahydro-1H-3-benzazepine-7,8-dione which (2 g) is reacted with methylmercaptan in methanol to give 6-methylthio-7,8-dihydroxy-1-(2-methylphenyl)-2,3,4,5-tetrahydro-1H-3-benzazepine hydrobromide.

Using m-methylstyrene oxide gives the 7,8-dihydroxy compound (mp 108°–110°), the 7,8-dione and finally 6-methylthio-7,8-dihydroxy-1-(3-methylphenyl)-2,3,4,5-tetrahydro-1H-3-benzazepine hydrobromide.

Using m-methoxystyrene oxide gives the 7,8-dihydroxy-m-hydroxyphenyl compound (mp 285° as the hydrobromide), the 7,8-dione and finally 6-methylthio-7,8-dihydroxy-1-(3-hydroxyphenyl)-2,3,4,5-tetrahydro-1H-3-benzazepine.

Using p-chlorostyrene oxide gives the 7,8-dihydroxy (mp 156°–164°), the dione and finally 6-methylthio-7,8-dihydroxy-1-(p-chlorophenyl)-2,3,45-tetrahydro-1H-3-benzazepine hydrobromide.

Using p-trifluoromethylstyrene oxide gives the 7,8-dihydroxy, the dione and finally 6-methylthio-7,8-dihydroxy-1-(p-trifluoromethylphenyl)-2,3,4,5-tetrahydro-1H-3-benzazepine hydrobromide.

EXAMPLE 6

A 3.3 g (0.019 mole) quantity of 7,8-dihydroxy-1-phenyl-2,3,4,5-tetrahydro-1H-3-benzazepine (free base) was slurried in 40 ml of dry acetone and 4.0 g of anhydrous potassium carbonate was added. The mixture was stirred under nitrogen, a small amount of ascorbic acid was added as antioxidant and the mixture chilled to 0° and 1.57 g (0.0129 mole) of allyl bromide was added. The mixture was stirred two to three hours in the cold and allowed to warm to ambient temperature and stir an additional twelve hours. The mixture was then heated to reflux for thirty minutes and cooled, poured into water and extracted with three portions of ethyl acetate. Concentration of the combined extracts gave 2.7 g of solid (71% crude yield). This was taken up in boiling ether and the solution allowed to stand for several hours. Filtration removed a small amount of precipitate and ethereal hydrogen chloride was then added to the filtrate to precipitate the hydrochloride salt which was isolated as an amorphous but non-hygroscopic solid, 2.0 g on filtration and drying. Trituration of the solid with hot ethyl acetate followed by recrystallization from ethanol-ethyl acetate gave 0.85 g of crystalline 3-allyl-7,8-dihydroxy-1-phenyl-2,3,4,5-tetrahydro-1H-3-benzazepine hydrochloride, mp 232°–234° (dec.).

This compound is reacted with quinone to give the 7,8-dione then with methylmercaptan in methanol to give 3-allyl-6-methylthio-7,8-dihydroxy-1-phenyl-2,3,4,5-tetrahydro-1H-3-benzazepine.

Substituting the 3-methyl, 3-butyl (mp 231°–234° as the hydrobromide) and 3-benzyl compounds gives 3-methyl-6-methylthio-7,8-dihydroxy-1-phenyl-2,3,4,5-tetrahydro-1H-3-benzazepine, 3-butyl-6-methylthio-7,8-dihydroxy-1-phenyl-2,3,4,5-tetrahydro-1H-3-benzazepine and 3-benzyl-6-methylthio-7,8-dihydroxy-1-phenyl-2,3,4,5-tetrahydro-1H-3-benzazepine substituting phenethyl bromide gives the 3-phenethyl-6-methylthio compound.

EXAMPLE 7

6-Methylthio-7,8-dihydroxy-1-phenyl-2,3,4,5-tetrahydro-1H-3-benzazepine (5 g) is oxidized with 2,3-dichloro-4,5-dicyano-1,4-benzoquinone in methanol at room temperature as in Example 1 to give 6-methylthio-1-phenyl-2,3,4,5-tetrahydro-1H-3-benzazepine-7,8-dione which (1 g) is reacted with methylmercaptan in methanol to give 6,9-dimethylthio-7,8-dihydroxy-1-phenyl-2,3,4,5-tetrahydro-1H-3-benzazepine.

EXAMPLE 8

7,8-Dimethoxy-1-phenyl-2,3,4,5-tetrahydro-1H-3-benzazepine (280 g, 0.75 mole) was dissolved in 1700 cc of acetic acid. Bromine (280 g, 1.75 mole) was added in a thin stream. The reaction was stirred for two hours. The precipitate, which formed after 1 hour, was collected and washed with ether. It was dissolved in boiling methanol and acetone was added to destroy the bromine excess. 6-Bromo-7,8-dimethoxy-1-phenyl-2,3,4,5-tetrahydro-1H-3-benzazepine hydrobromide was allowed to crystallize from the methanol and a second crop was obtained by adding ether to the mother liquor. Yield 298 g. 77% m.p. 236–238%. This bromination may be applied to any 7,8-dialkoxy or alkanoyloxybenzazepine having a free 6-position.

The hydrobromide was shaken in a mixture of excess 10% sodium hydroxide and methylene chloride. The organic layer was separated, dried and evaporated to give a solid base which was crystallized from toluene-hexane; m.p. 125°–128°, yield 238 g (97%).

6-Bromo-7,8-dimethoxy-1-phenyl-3-trifluoro-acetyl-2,3,4,5-tetrahydro-1H-3-benzazepine (5 g, prepared by reaction of trifluoroacetic anhydride in benzene on the N-hydrogen compound prepared above) is reacted with an excess of butyl lithium in ether at −78° to give the 6-lithium salt-3-trifluoroacetylbutyl-lithium adduct. This intermediate is reacted without isolation with an excess of dimethyldisulfide in ether at reflux overnight. After hydrolysis with water, 6-methylthio-7,8-dimethoxy-1-phenyl-2,3,4,5-tetrahydro-1H-3-benzazepine is obtained. Other disulfides especially di(trifluoromethyl)disulfide may be substituted as well as other N-alkylated or N-acylated benzazepines.

EXAMPLE 9

2-(2-Methylthio-3,4-dimethoxyphenyl)-ethylamine was prepared from 2-chloroveratraldehyde [L. C. Raiford and R. P. Perry, J Org. Chem., 7, 354 (1942)] by first forming the ethylene acetal (from ethylene glycol with acid catalysis and azeotropic removal of water) and then the Grignard reagent (magnesium and dibromoethane in refluxing benzene) which was reacted with dimethyldisulfide in refluxing benzene. Hydrolysis of the acetal (refluxing aqueous acetic acid) give 2-methylthioveratraldehyde which was condensed with nitromethane and then reduced with lithium aluminum hydride to give the desired phenethylamine.

2-(2-Methylthio-3,4-dimethoxyphenyl)ethylamine (26 g) is heated to 115° in an oil bath. Styrene oxide (14.4 g) is added and the reaction is heated for 1 hour. After cooling to ∼30°, hexane-ethyl acetate is used to produce N-[(2-hydroxy-2-phenylethyl)]-N-[2-(2'-methylthio-3',4'-dimethoxyphenyl)ethyl]amine.

The methylthio containing hydroxyphenethylamine (15 g) is dissolved in a 2:1 mixture of acetic acid/conc.

hydrochloric acid. The reaction is refluxed 2 hours. After cooling most of the volatiles are stripped off and the residue is poured into water. It is made basic with 50% sodium bicarbonate and extracted with ethyl acetate twice. The extracts are washed with brine, dried and evaporated to give 6-methylthio-7,8-dimethoxy-1-phenyl-2,3,4,5-tetrahydro-1H-3-benzazepine.

EXAMPLE 10

7,8-Dihydroxy-6-methylthio-1-phenyl-2,3,4,5-tetrahydro-1H-3-benzazepine (5.0 g) is suspended in 50 ml of benzene. Trifluoroacetic anhydride (15 g) is added dropwise rapidly. The solution is stirred an additional hour and then the volatiles are stripped off, leaving the N,O,O-tris-trifluoroacetyl derivatives. This is added directly to 50 ml of methanol and hydrogen chloride gas is bubbled in for a few minutes. The reaction is stirred for 2 hours and the solvent stripped off, leaving a residue of 7,8-dihydroxy-6-methylthio-1-phenyl-3-trifluoroacetyl-2,3,4,5-tetrahydro-1H-3-benzazepine.

The N-trifluoroacetyldihydroxy compound (3 g) is reacted with an excess of methyl iodide in the presence of sodium carbonate in aqueous ethanol at room temperature. The crude 7,8-dimethoxy-6-dimethyl sulfonium iodide is isolated by evaporation then heated at reflux in brine solution for 2 hours. The folatiles are evaporated and the residue recrystallized to give 7,8-dimethoxy-6-methylthio-1-phenyl-3-trifluoroacetyl-2,3,4,5-tetrahydro-1H-3-benzazepine. The N-acyl group is removed by treatment with 5% sodium hydroxide in aqueous methanol at room temperature to give 7,8-dimethoxy-6-methylthio-1-phenyl-2,3,4,5-tetrahydro-1H-3-benzazepine.

EXAMPLE 11

7,8-Dihydroxy-6-methylthio-1-phenyl-2,3,4,5-tetra-1H-3-benzazepine hydrobromide (5 g) is dissolved in trifluoroacetic acid and reacted with a stoichiometric quantity of acetyl chloride in the cold. The reaction mixture is quenched in brine and extracted with ethyl acetate to give the desired 7,8-diacetoxy derivative. Substituting other alkanoyl anhydrides or chlorides gives various 7,8-dialkanoyl derivative.

EXAMPLE 12

A solution of 7.10 g (18.6 mmoles) of 7,8-dihydroxy-1-phenyl-6-methylthio-2,3,4,5-tetrahydro-1H-3-benzazepine, hydrobromide in 120 ml of aqueous dimethylformamide at 0° under an argon atmosphere is basified to pH 10.0 with 10% sodium hydroxide solution. To this cold mixture is added 13.0 (76 mmoles) of carbobenzoxy chloride in small portions over 15 minutes with concomitant addition of 10% alkali so as to maintain a pH of 10 to 10.5. The reaction is allowed to warm to room temperature after stirring at 0° for 1½ hours. The mixture is diluted with saturated salt and extracted with three portions of ethyl acetate. The combined organic extract is backwashed twice with saturated salt. The dried extract is concentrated in vacuo and heated at 75°/0.1 mm Hg to remove any benzyl alcohol.

The residue is taken up in 50 ml of glacial acetic acid, cooled to 15° and treated with 14 ml of 40% peracetic acid over 5 minutes at 10°–15°. The solution is allowed to warm to room temperature. Further treatment with portions of 40% peracetic acid to complete conversion to the sulfone are often needed. The reaction is quenched in 800 ml of water and extracted with three portions of ethyl acetate. The combined organic layers are washed with two portions of saturated salt, three portions of 5% bicarbonate and two portions of saturated salt. The extracts are dried, treated with decolorizing charcoal, concentrated in vacuo and pumped free of solvent to give 12 g of N-carbobenzoxy-6-methylsulfonyl compound.

This protected sulfone is treated with 70 ml of 38% hydrobromic acid in glacial acetic acid at room temperature for 2 hours. The solution is added dropwise into 1 l. of rapidly stirred anhydrous diethyl ether over 40 minutes. The solids are allowed to settle and the supernatant decanted. The precipitate is washed several times with fresh ether and dried under a nitrogen stream to give the hydrobromide salt of 7,8-dihydroxy-6-methylsulfonyl-1-phenyl-2,3,4,5-tetrahydro-1H-3-benzazepine.

Using variations of this method with other starting materials the 6-trifluoromethylsulfonyl containing compound and other products of this invention can be prepared.

EXAMPLE 13

A solution of 8.6 g (20 mm) of 3-acetyl-7,8-diacetoxy-1-phenyl-6-methylthio-2,3,4,5-tetrahydro-1H-3-benzazepine (prepared by reacting the dihydroxy parent with an excess of acetic anhydride in pyridine at room temperature) in 40 ml of methanol at −5° is treated with 40 ml of 0.52 M sodium periodate (20.8 mm) dropwise over 15 minutes at 0°. The mixture is cooled overnight, then filtered to give a solid which is washed with methylene chloride. The organic extracts are combined, dried and evaporated in vacuo. The residue is heated at reflux in ethanolic hydrochloric acid overnight. The volatiles are removed and the residue taken up in water. Neutralization with ammonia and extraction with ethyl acetate gives the desired 7,8-dihydroxy-6-methylsulfinyl-1-phenyl-2,3,4,5-tetrahydro-1H-3-benzazepine. The hydrochloride salt is formed by treatment with ethereal hydrogen chloride.

EXAMPLE 14

| Ingredients | Mg. per Capsule |
|---|---|
| 6-Methylthio-7,8-dihydroxy-1-phenyl-2,3,4,5-tetrahydro-1H-3-benzazepine (as an acid addition salt) | 125 (free base) |
| Magnesium stearate | 2 |
| Lactose | 200 |

The above ingredients are thoroughly mixed and placed into hard gelatin capsules. Such capsules are administered orally to subjects in need of treatment from 1–5 times daily to induce dopaminergic or antiparkinsonism activity.

EXAMPLE 15

| Ingredients | Mg. per Tablet |
|---|---|
| 9-Methylthio-7,8-dihydroxy-1-phenyl-2,3,4,5-tetrahydro-1H-3-benzazepine (as an acid addition salt) | 200 (free base) |
| Corn starch | 30 |
| Polyvinyl pyrrolidone | 12 |
| Corn starch | 16 |
| Magnesium stearate | 3 |

The first two ingredients are thoroughly mixed and granulated. The granules obtained are dried, mixed with the remaining corn starch and magnesium stearate, and compressed into tablets.

The capsules or tablets thusly prepared are administered orally to an animal or human requiring stimulation of central dopamine receptors such as to treat the symptom of Parkison's disease within the dose ranges set forth hereinabove. Similarly other compounds of Formula I and the illustrative examples can be formulated in the same manner to give pharmaceutical compositions useful in the methods of this invention based on the chemical characteristics and relative biological activity using the test methods outlined.

A subgroup of the new compounds of this invention have also been unexpectedly found to demonstrate dopamine antagonist activity in standard pharmacological procedures involving non-brain damaged animals in contrast to the dopaminergic test in brain lesioned animals outlined above. Such compounds are especially those of Formula I which have enough hydrocarbon substitution to enhance lipophilicity, such as those in which the carbon content of R plus $R_1$ is at least 2. Any of the compounds of Formula I can be put into the test described below, however, to determine if they have dopamine antagonist activity. Especially active are 6-methylthio-3-methyl-1-phenyl-2,3,4,5-tetrahydro-1H-3-benzazepine ($ED_{50}=0.3$ mg/kg) or 1-phenyl-6-n-butylthio-2,3,4,5-tetrahydro-1H-3-benzazepine ($ED_{50}=2.1$ mg/kg i.p.). The 6-isopropylthio congener gives a 40% block at 10 mg/kg i.p. while the 6-methylthio compound gives no such activity at 10 mg/kg i.p.

The test procedure for antagonist activity is as follows:

The antipsychotic activity of the compounds of this invention is measured by antagonism of avoidance acquisition in rats. In this pharmacological procedure, naive male rats are given either a test compound or saline at a suitable time period prior to testing. The rats are then placed in a dark soudproof box with a gird floor through which foot-shock is delivered. Trials begin a 30-second intervals. The beginning of each trial is signaled by a light and a buzzer which continues for 10 seconds, at which time foot-shock is added for an additional 15 seconds. In each trail a single lever press by the animal terminates the sequence. Evaluation of drug activity is based on the number of trails in which the animals fail to avoid or fail to escape footshock during the last 40 trials of a 100 trial, 50-minute session. The $ED_{50}$ is defined as that dose of drug calculated to reduce the number of avoidance responses during the last 40 trials to 50% of the (pooled) control value. Antagonism of avoidance acquisitions in the rat is a useful pharmacological procedure for assessing antipsychotic activity.

Antagonist compounds are as stated useful as antipsychotic agents such as chlorpromazine (1.5 mg/kg).

In addition to the central dopaminergic activities mentioned above the 6-methylthio-3-methyl congener has an $RD_{500}$ of 0.098 mg/kg i.p., $RD_{1000}$ of 7.4 mg/kg p.o.; 6-ethylthio, 0.25 mg/kg i.p.; 9-methylthio-1-o-methylphenyl 786±131 at 10 mg/kg i.p.; 6-methylthio-1-o-methylphenyl, 0.14 mg/kg i.p.; 6-methylthio-1-m-chlorophenyl, 0.42 i.p.; 6-methylthio-O,O-diacetyl, 1268±318 at 0.3 mg/kg i.p.; 6-methylthio-1-p-hydroxyphenyl 127±55 at 10 i.p.; 6,9-dimethylthio, 51±22 at 10 mg/kg i.p.

What is claimed is:

1. A compound of the formula:

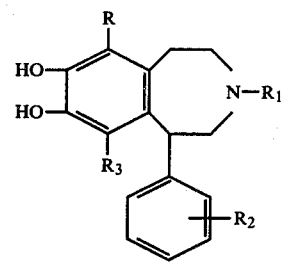

in which:

R is hydrogen, alkylthio, alkyl sulfinyl, alkyl sulfonyl, trifluoromethylthio, trifluoromethylsulfinyl or trifluoromethylsulfonyl and $R_3$ is hydrogen or, when R is hydrogen or alkylthio, alkylthio at least one of R and $R_3$ being a group other than hydrogen;

$R_1$ is hydrogen, alkyl or alkenyl of 3-5 carbons; and $R_2$ is hydrogen, halo, trifluoromethyl, methyl, methoxy or hydroxy; ether or ester derivatives thereof having the same O-alkyl or O-alkanoyl in place of both the 7,8-dihydroxy groups and the pharmaceutically acceptable nontoxic salts thereof, said alkyl groups wherever present being of 1-5 carbons and said alkanoyl groups whenever present being of 2-5 carbons.

2. The compound of claim 1 in which $R_3$ is hydrogen and R is methylthio or trifluoromethylthio.

3. The compound of claim 1 in which $R_3$ is methylthio and R and $R_1$ are hydrogen.

4. The compound of claim 3 in which $R_2$ is hydrogen.

5. The compound of claim 1 in which $R_1$ and $R_3$ are hydrogen, R is methylthio or trifluoromethylthio and $R_2$ is hydrogen, chloro, methyl, trifluoromethyl, methoxy or hydroxy.

6. The compound of claim 1 in which R is methylthio, $R_3$ is hydrogen and $R_1$ and $R_2$ are hydrogen.

7. The compound of claim 6 in which the compound is in the form of a nontoxic pharmaceutically acceptable acid addition salt.

8. The compound of claim 6 in which the compound is in the form of the hydrobromide.

9. A method of inducing central dopaminergic activity in an animal or human subject in need thereof comprising administering orally or by injection a therapeutically effective quantity of a compound of claim 1.

10. The method of claim 9 in which the induced activity is useful in treating parkinsonism.

11. The method of claim 10 in which the compound is 6-methylthio-7,8-dihydroxy-1-phenyl-1H-3-benzazepine or its nontoxic pharmaceutically acceptable salts.

12. A pharmaceutical composition for treating the symptons of Parkinson's disease comprising a therapeutically effective quantity of a compound of claim 1 and a carrier.

13. The composition of claim 12 in which the compound is 6-methylthio-7,8-dihydroxy-1-phenyl-1H-3-benzazepine or its nontoxic pharmaceutically acceptable acid addition salts.

14. The compound of claim 1 in which one of R and $R_3$ is methylthio and the other is hydrogen, $R_1$ is methyl and $R_2$ is hydrogen.

15. The compound of claim 1 in which R is methylthio, $R_2$ and $R_3$ are hydrogen and $R_1$ is methyl.

16. The compound of claim 1 in which $R_3$ is methylthio, R and $R_2$ are hydrogen and $R_1$ is methyl.

17. The compound of claim 1 in which the carbon atom content of R and $R_1$ is at least 2.

* * * * *